United States Patent [19]

Berges

[11] 4,210,587
[45] Jul. 1, 1980

[54] 7-ACYLAMINO-3-[1-[2-(CARBOXYMETHYLAMINO)ETHYL]TETRAZOL-5-YLTHIO METHYL]-3-CEPHEM-4-CARBOXYLIC ACIDS

[75] Inventor: David A. Berges, Wayne, Pa.

[73] Assignee: SmithKline Corporation, Philadelphia, Pa.

[21] Appl. No.: 921,921

[22] Filed: Jul. 3, 1978

Related U.S. Application Data

[62] Division of Ser. No. 809,585, Jun. 24, 1977, Pat. No. 4,117,125.

[51] Int. Cl.$^2$ .............................. C07D 257/04
[52] U.S. Cl. ..................................... 548/251

[58] Field of Search ................. 260/308 D; 544/26

[56] References Cited

U.S. PATENT DOCUMENTS 4,110,338  8/1978  Kamiya et al. ............... 260/308 D

*Primary Examiner*—Donald G. Daus
*Assistant Examiner*—D. B. Springer
*Attorney, Agent, or Firm*—Joseph A. Marlino; Richard D. Foggio; William H. Edgerton

[57] ABSTRACT

Novel cephalosporins having various acyl substituents at the 7-position and a carboxymethylaminoethyl substituted tetrazolylthiomethyl group at the 3-position of the cephem nucleus are prepared. These compounds have antibacterial activity.

3 Claims, No Drawings

7-ACYLAMINO-3-[1-[2-(CARBOXYME-THYLAMINO)ETHYL]TETRAZOL-5-YLTHIO METHYL]-3-CEPHEM-4-CARBOXYLIC ACIDS

This is a division of application Ser. No. 809,585 filed June 24, 1977, now U.S. Patent No. 4,117,125.

This invention relates to a new series of cephalosporin compounds having antibacterial activity and to intermediates useful for preparing them. The structures of the new compounds are characterized by having at the 3-position of the cephalosporin nucleus an amino acid substituted tetrazole group.

Exemplary of the compounds of this invention are those represented by the following structural formula:

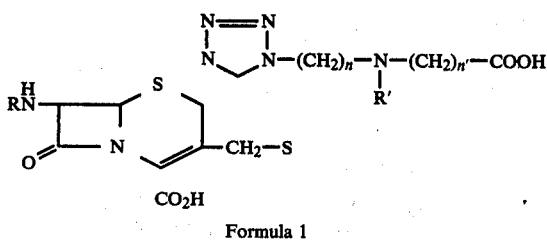

Formula 1 in which R represents a pharmaceutically acceptable acyl group known to be of utility as a substituent on the 7-amino group in the structures of known or prior art cephalosporins or on the 6-amino group in the structures of known or prior art penicillins.

Representative acyl substituents are:

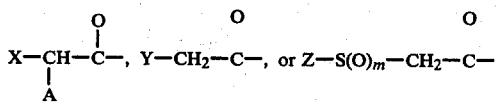

wherein:
X is thienyl, furyl, phenyl or phenyl monosubstituted with hydroxy, hydroxymethyl, formamido or ureido;
A is $NH_2$, OH, COOH, $SO_3H$, formyloxy or, when the α-C-hydrogen is absent, methoxyimino;
Y is cyano, sydnone, pyridone, thienyl, o-aminomethylphenyl, phenyl or tetrazolyl;
Z is methyl, trifluoromethyl, trifluoroethyl, pyridyl or cyanomethyl;
m is zero to two;
R' is hydrogen or lower alkyl having from one to four carbons;
n is two to four, preferably two; and
n' is one to four, preferably one.

Each of the three partial structures above represent subgeneric groups of compounds covered by this invention.

Representative 7-acylamino substituents of the compounds of Formula 1 are listed below:
α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido α-sulfophenylacetamido
methylsulfonylacetamido
cyanomethylthioacetamido
3-sydnoneacetamido
1-tetrazolylacetamido
2-thienylacetamido
α(Z)-(methoxyimino)-2-furanacetamido
4-pyridylthioacetamido
o-aminomethylphenylacetamido Others together with N-acylation procedures may be found in *Cephalosporins and Penicillins*, Flynn, Academic Press, 1972; U.S. Pat. Nos. 2,721,196 and 3,953,424; Belgian Pat. No. 832,725; German Pat. Nos. 2,127,285 and 2,406,165.

It will be recognized that the carboxylic acid group present such as at position 4 and on the tetrazole of the compounds of Formula 1 may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such ester derivatives are included within the scope of this invention.

Also covered in this invention are the pharmaceutically acceptable, nontoxic derivatives of the compounds of Formula 1 from which they derive utility: the salts, easily split ester or ether derivatives of either a carboxy or hydroxy function, amide derivatives at an amino group contained in a 7-phenylglycylamino group, for example, the furyl-, pyranyl-, oxolanyl- or oxiranyl-carbonyl amides (i.e. Belgian Pat. No. 835,295), the solvates such as hydrates, glycolates or alcoholates. As examples of these, one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine.

Other known cephalosporin modifications can be made by known synthetic procedures such as introduction of an α-methoxy group at position 7, preferably at the stage of the 7-aminocephalosporanic acid reactants (IV) disclosed below, prior to N-acylation. Optical isomers are also possible such as with the mandeloyl or phenylglycyl substituents at 7. The D-forms of these subgeneric groups are preferred.

It will be apparent to those skilled in the art that the secondary amino function on the amino acid-substituted-tetrazolyl portion of the structures of Formula 1 can be converted by methods well known to amino acid art to N-lower alkyl or N-lower alkanoyl derivatives of 1-6 carbons. The N-lower alkyl derivatives are best prepared by N-monoalkylation of the 1-[[[(carbalkoxy)alkyl]amino]alkyl]-5-[(4-methoxybenzyl)thio]-1H-tetrazole intermediate which tertiary amine is then used in the process of Example 1 hereafter. The N-acyl derivatives (Formula 1 when R' is acyl) are prepared by N-acylation of the compounds of Formula 1 when R' is hydrogen and any carboxylic acid groups are suitably protected as known in the art.

The compounds of this invention are most conveniently prepared by a displacement of the acetoxy group of a known 7-acylaminocephalosporanic acid (II) by, for example, 1-[2-(carboxymethylamino)ethyl]-1,4-dihydro-5H-tetrazole-5-thione (III) usually as an alkali metal salt. Alternatively, a similar displacement with the thione can be run on 7-aminocephalosporanic acid to give 7-amino-3-[1-[2-(carboxymethylamino)ethyl]tetrazol-5-ylthiomethyl]-3-cephem-4-carboxylic acid (IV), a new intermediate, which may then be N-acylated as known to the art as described above. Suitable protective groups may be used in either method as is known in the art (see "Protective Groups in Organic Chemistry", J. F. W. McOmie, Plenum Press, 1973, Chapters 2 and 3 for use of amino, carboxy, sulfo or hydroxyl protective groups).

For example, the t-butyl (for COOH), or t-butoxycarbonyl (for NH$_2$) groups are easily removed by treatment with trifluoroacetic acid.

The 1-aminoacid substituted tetrazole-5-thiones exposed in their tautomeric forms by Formula III are new compounds and are part of this invention.

effective, nontoxic amount of the new cephalosporin compound is the preferred route of administration.

The compounds of Formula 1 are formulated and administered in the same manner as other prior art cephalosporins such as cephazolin or cephalothin. The dosage regimen comprises administration, preferably by injection, of an active but nontoxic quantity of a compound of Formula 1 selected from the dosage unit range of from about 250 mg. to 600 mg. with the total daily dosage regimen being from about 750 mg. to 6 g. The precise dosages are dependent upon the age and weight of the subject and on the susceptibility of the infection being treated to each individual. These can be determined by those skilled in the art based on the data disclosed herein compared with that available to the art attained with the known cephalosporins outlined herebefore.

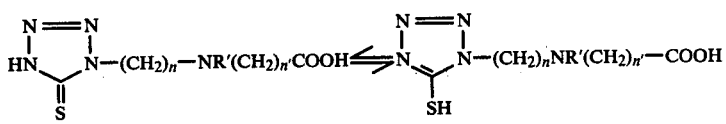

III n, n', and R' are as defined above.

Also included in this invention are the alkali metal and ammonium salts of III.

The compounds of Formula 1 have antibacterial activity against both Gram positive and Gram negative bacteria with minimum inhibitory concentrations (MIC's) in vitro from 0.2 to 200 μg/ml. Test results for 7-D-mandelamido-3-[1[2-(carboxymethylamino)ethyl]-tetrazol-5-ylthiomethyl]-3-cephem-4-carboxylic acid hydrate (A) are:

|  | A | Cefazolin | Cephalothin |
|---|---|---|---|
| S. aureus HH 127 | 3.1 | 0.4 | 0.2 |
| S. aureus SK 23390 | 1.6 | 0.2 | ≦0.1 |
| S. aureus villaluz SK 70390 | 100 | 100 | 50 |
| Strep. faecalis HH 34358 | 50 | 6.3 | 12.5 |
| E. coli SK 12140 | 0.8 | 0.8 | 3.1 |
| E. coli HH 33779 | 0.8 | 0.8 | 6.3 |
| Kleb. pneumo. SK 4200 | 0.4 | 0.8 | 1.6 |
| Kleb. pneumo. SK 1200 | 0.4 | 0.8 | 1.6 |
| Salmonella ATCC 12176 | 0.2 | 0.8 | 0.8 |
| Pseudo. aeru. HH 63 | ≧200 | ≧200 | ≧200 |
| Serratia marc. ATCC 13880 | 3.1 | 200 | ≧200 |
| Proteus morgani 179 | 3.1 | 200 | 200 |
| Entero. aerog. ATCC 13048 | 1.6 | 1.6 | 12.5 |
| Entero. cloacae HH 31254 | 0.8 | 0.8 | 6.3 |
| Proteus mirabilis PN-444 | 0.8 | 3.1 | 6.3 |

Compound A gave an ED$_{50}$ in mice of 0.39 mg/kg (s.c.) and 7.2 mg/kg (p.o.) against E. coli, and 0.39 mg/kg against Kleb. pneumo. (s.c.) and 4 mg/kg (p.o.). Cephalexin gives comparable values of 15.7 (s.c.) and 25 (p.o.) against E. coli and 21.5 mg/kg (s.c.) and 18 mg/kg (p.o.) against Kleb. pneumo.

Pharmaceutical compositions having antibacterial activity which comprise a pharmaceutical carrier containing an active but nontoxic quantity of a compound of Formula 1 as well as methods of combatting bacterial infections by administering such a composition to an infected animal or human host in a nontoxic amount sufficient to combat such infections are also objects of this invention. The administration may be orally or by parenteral injection such as subcutaneously, intramuscularly or intravenously. The injection of suitably prepared sterile solutions or suspensions containing an The following examples illustrate the invention but are not to be construed as limiting the scope thereof. Temperatures are in degrees Centigrade (°C.) unless otherwise stated.

EXAMPLE 1

A mixture of 21.5 g. (11.4 mmol) of 1-[2-(acetylamino)ethyl]-1,4-dihydro-5H-tetrazole-5-thione in 300 ml. of 6 N hydrochloric acid was heated at reflux for 3.5 hours. The mixture was filtered after cooling to room temperature. The filtrate was concentrated to small volume. The residual liquid was diluted with i-propanol. The solid which precipitated was filtered, washed and dried in vacuo to give 13.7 g. of 1-(2-aminoethyl)-1,4-dihydro-5H-tetrazole-5-thione, hydrochloride (66.1% yield) mp 232°–233.5° C.

To a solution of 22.8 g. (12.5 mmol) of 1-(2-aminoethyl)-1,4-dihydro-5H-tetrazole-5-thione, hydrochloride in 100 ml. of N,N-dimethylformamide and 100 ml. of acetone was added 34.3 ml. (25 mmol) of triethylamine. To the resulting suspension was added slowly a solution of 19.5 g. (12.5 mmol) of p-methoxybenzyl chloride in 30 ml. of acetone. After stirring at room temperature for 15 hours, the mixture was filtered. The filtrate was evaporated to dryness. The residue was taken up in 350 ml. of 5% NaHCO$_3$, and extracted with ethyl acetate. The combined extract was dried (MgSO$_4$) and evaporated to dryness to give an oil which was chromatographed on a silica gel column, eluting with a gradient of 5–10% ethanol in chloroform. Fractions containing product by thin layer chromatography were pooled, and evaporated to dryness to give 1-(2-aminoethyl)-5-(4-methoxybenzylthio)-1H-tetrazole as a brown oil (26 g., 80%). An analytical sample of the crystalline amine hydrochloride (mp 148°–150°) was obtained by treating the product with an ethereal HCl solution.

To a solution of 15.0 g. (56 mmol) of 1-(2-aminoethyl)-5-[(4-methoxybenzyl)thio]-1H-tetrazole in 70 ml. of dry tetrahydrofuran was added 7.7 ml. (56 mmol) of triethylamine, and 6.2 ml. (56 mmol) of ethyl bromoacetate. After stirring at room temperature for 15 hours, the mixture was filtered, and the filtrate was evaporated in vacuo to dryness. The residue was dissolved in 70 ml. of chloroform and decolorized with charcoal. The filtrate was chromatographed on silica gel, eluting with a gradient of 0–15% ethyl acetate in chloroform. Fractions containing product by thin layer chromatography were pooled and evaporated to dryness to give 12.5 g. (62% yield) of 1-[2-[[(carbethoxy)methyl]amino]ethyl]-5-[(4-methoxybenzyl)thio]-1H-tetrazole as a brown oil.

To a solution of 12.5 g. (35.6 mmol) 1-[2-[[carbethoxy)methyl]amino]ethyl]-5-[(4-methoxybenzyl)thio]-1H-tetrazole in 250 ml. of methanol and 65 ml. of water was added a solution of 25.5 g. (80 mmol) of mercuric acetate in 80 ml. of water. The mixture was stirred at room temperature for 15 hours and at reflux for 1 hour. After thorough cooling, the mixture was treated with hydrogen sulfide gas for 1.5 hours. The dark mixture was heated over a steam bath for 1.5 hours and filtered. The filtrate was evaporated in vacuo to dryness. The residue was recrystallized from ethyl acetate to give 5.9 g. of 1-[2-[(carboxymethyl)amino]ethyl]-1,4-dihydro-5H-tetrazole-5-thione (82.8% yield) mp 215°–220° dec.

To a solution of 420 mg. (5 mmol) of sodium bicarbonate in 25 ml. of water was added 1.01 g. (5 mmol) of 1-[2-[(carboxymethyl)amino]ethyl]-1,4-dihydro-5H-tetrazole-5-thione. After $CO_2$ gas evolution had ceased, 2.6 g. (6 mmol) of 7-D-mandelamidocephalosporanic acid, sodium salt, was added to the solution. The mixture was stirred and heated at 65° C., while pH was maintained at 7.0 by addition of a 5% $NaHCO_3$ solution. After 2 hours the mixture was filtered. The filtrate was applied to a Biogel P-2 (100–200 mesh) column, eluting with de-ionized water. Fractions containing product by thin layer chromatography were pooled, concentrated to small volume, and applied to a cellulose column. A mixture of acetonitrile and water (8 to 2) was used as chromatographic solvent. The eluate that contained product was evaporated to dryness. The residue was dissolved in deionized water and solution was lyophilized to give 290 mg. of 7-D-mandelamido-3-[1-[2-[(carboxymethyl)amino]ethyl]-tetrazole-5-ylthiomethyl]-3-cephem-4-carboxylic acid (10% yield) mp 170°–173° C. dec.

EXAMPLE 2

Substituting in the above procedure equimolar quantities of 1-[3-(acetylamino)propyl]-1,4-dihydro-5H-tetrazole-5-thione or 1-[4-(acetylamino)butyl]-1,4-dihydro-5H-tetrazole-5-thione (prepared as described in the art from N-(3-aminopropyl)acetamide and N-(4-aminobutyl)acetamide respectively gives 7-(D-mandelamido)-3-[1-3-[(carboxymethyl)amino]propyl]tetrazole-5-ylthiomethyl]-3-cephem-4-carboxylic acid and 7-(D-mandelamido)-3-[1-[4[(carboxymethyl)amino]butyl]tetrazol-5-ylthiomethyl]-3-cephem-4-carboxylic acid. Substituting ethyl 4-bromobutyrate in place of ethyl bromoacetate above gives 1-[2-[(B-carboxypropyl)amino]-ethyl]-1,4-dihydro-5H-tetrazole-5-thione and 7-(D-mandelamido)-3-[1-[2-[(3-carboxypropyl)amino]ethyl]-1H-tetrazol-5-ylthiomethyl]-3-cephem-4-carboxylic acid.

EXAMPLE 3

A mixture of 5.22 g. (10.0 mmol) of 7-[D-α-(t-butoxycarbonyl)amino-α-(4-hydroxyphenyl)acetamido]-cephalosporanic acid and an excess (15.0 mmol) of 1-[2-[(carboxymethyl)amino]ethyl]-1,4-dihydro-5H-tetrazole-5-thione in 75 ml. of water is treated with sufficient sodium bicarbonate to give a solution of pH 7.0. The solution is heated at 70° for 3 hours, cooled, and added to a XAD-7 resin column. Elution with water and then methanol followed by evaporation of the product-containing fractions gives the t-boc derivative of the desired compound. This derivative is stirred at 25° C. with 25 ml. of trifluoroacetic acid and 25 ml. of 1,3-dimethoxybenzene for 2 hours. The mixture is evaporated to dryness, either added to the residue and the precipitated salt collected. This is dissolved in water and two molecular equivalents of sodium bicarbonate are added. The solution is lyophilized and then triturated with acetone to give 7-[D-α-amino-α-(4-hydroxyphenyl)acetamido]-3-[1-[2-[(carboxymethyl)amino]ethyl]tetrazol-5-ylthiomethyl]-3-cephem-4-carboxylic acid. Similar treatment of the t-boc derivative of the 7-D-(α-amino-α-phenylacetamido)cephalosporanic acid gives the corresponding 7-D-(α-amino-α-phenylacetamido)-3-[1-[2-[(carboxymethyl)amino]ethyl]tetrazol-5-ylthiomethyl]-3-cephem-4-carboxylic acid.

EXAMPLE 4

A mixture of an excess (12.2 mmol) of 1-[2-[(carboxymethyl)amino]ethyl]-1,4-dihydro-5H-tetrazole-5-thione, 32.5 mmol of sodium bicarbonate and 8.1 mmol of 7-trifluoromethylthioacetamidocephalosporanic acid in 50 ml. of water is stirred at 70° for 5 hours. The reaction mixture is cooled and passed over XAD-2 resin with water and methanol as eluants. The product-containing fractions are evaporated to dryness to give a residue which is dissolved in a small amount of water and lyophilized to give 7-trifluoromethylthioacetamido-3-[1-[2-[(carboxymethylamino]ethyl]tetrazol-5-ylthiomethyl]-3-cephem-4-carboxylic acid disodium salt. Substituting 7-(2-thienylacetamido)cephalosporanic acid gives 7-(2-thienylacetamido)-3-[1-[2-[(carboxymethyl)amino]ethyl]tetrazol-5-ylthiomethyl]-3-cephem-4-carboxylic acid disodium salt.

Stoichiometric quantities of cephalosporanic acids having the individual 7-acylamino substituent listed hereabove may be substituted in Examples 1–3 with variations which will be obvious to those skilled in this art.

EXAMPLE 5

To a solution of 10 mmol of 1-[2-[[(carbethoxy)methyl]amino]ethyl]-5-[(4-methoxybenzyl)thio]-1H-tetrazole and 10 mmol of triethylamine in 20 ml. of dry tetrahydrofuran is added 10 mmol of methyliodide. After stirring at room temperature for 24 hours, the mixture is filtered. The filtrate is stripped in vacuo to dryness, and the residue is dissolved in chloroform and chromatographed on silica gel eluting with a gradient of ethylacetate in chloroform. Evaporation of the product-containing fractions gives 1-[2-[[(carbethoxy)methyl]methylamino]ethyl]-5-[(4-methoxylbenzyl)thio]-1H-tetrazole. Deblocking with mercuric acetate as above gives 1-[2-[(carboxymethyl)methylamino]ethyl]-1,4-dihydro-5H-tetrazole-5-thione which when substituted in the reaction with 7-D-mandelamidocephalosporanic acid gives 7-D-mandelamido-3-[1-[2-[(carboxymethyl)methylamino]ethyl]-tetrazol-5-ylthiomethyl]-3-cephem-4-carboxylic acid.

EXAMPLE 6

An injectable pharmaceutical composition is formed by adding sterile saline solution (2 ml.) to 500 mg. of the product of Example 1. This material is injected parenterally four times daily to a human patient infected with susceptible bacteria. Other compounds of this invention may be similarly used.

EXAMPLE 7

An aqueous solution of 4.27 g. (0.0096 mmol) of 7-[α(Z)-(methoxyimino)-2-furanacetamido]cephalosporanic acid sodium salt, 1.78 g. (0.0212 mmol) of sodium bicarbonate, and 2.15 g. (0.106 mmol) of 1-[2-[(carboxymethyl)amino]ethyl]-1,4-dihydro-5H-tetrazole-5-thione is heated at 65° C. for 6 hours during which time the pH is maintained at 7.6–7.8 with dilute sodium bicarbonate. After cooling, the reaction mixture is purified on an XAD-2 column as described in Example 4 to give a lyophilized product, 7-[α(Z)-(methoxyimino)-2-furanacetamido]-3-[1-[2-[(carboxymethyl)amino]-ethyl]-tetrazole-5-ylthiomethyl]-3-cephem-4-carboxylic acid, disodium salt.

What is claimed is:

1. A compound of the formula:

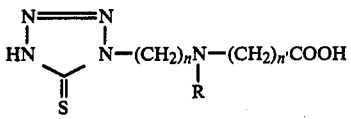

in which:
R is lower alkyl having from one to four carbons or hydrogen;
n is two to four;
n' is one to four; or its alkali metal and ammonium salts.

2. The compound of claim 1 being 1-[2-[(carboxymethyl)amino]ethyl]-1,4-dihydro-5H-tetrazole-5-thione.

3. The compound of claim 2 being the sodium salt.

* * * * *